US012697294B2

(12) United States Patent
Bai et al.

(10) Patent No.: US 12,697,294 B2
(45) **Date of Patent: *Aug. 4, 2026**

(54) HAIR OIL FORMULATION

(71) Applicants: Dow Global Technologies LLC, Midland, MI (US); Rohm and Haas Company, Collegeville, PA (US)

(72) Inventors: Lu Bai, Novi, MI (US); Nikhil J. Fernandes, Philadelphia, PA (US); Emmett M. Partain, III, Bound Brook, NJ (US); Lyndsay M. Leal, Spring City, PA (US); Binghe Gu, Midland, MI (US); Jennifer P. Todd, Willow Grove, PA (US); Peilin Yang, Pearland, TX (US)

(73) Assignees: DOW GLOBAL TECHNOLOGIES LLC, Midland, MI (US); ROHM AND HAAS COMPANY, Collegeville, PA (US)

( * ) Notice: Subject to any disclaimer, the term of this patent is extended or adjusted under 35 U.S.C. 154(b) by 614 days.

This patent is subject to a terminal disclaimer.

(21) Appl. No.: 17/798,213

(22) PCT Filed: Mar. 17, 2021

(86) PCT No.: PCT/US2021/022655

§ 371 (c)(1),
(2) Date: Aug. 8, 2022

(87) PCT Pub. No.: WO2021/194809

PCT Pub. Date: Sep. 30, 2021

(65) Prior Publication Data

US 2023/0117582 A1 Apr. 20, 2023

Related U.S. Application Data

(60) Provisional application No. 62/993,781, filed on Mar. 24, 2020.

(51) Int. Cl.

| | |
|---|---|
| ***A61K 8/73*** | (2006.01) |
| ***A61K 8/92*** | (2006.01) |
| ***A61Q 5/02*** | (2006.01) |
| ***A61Q 5/12*** | (2006.01) |
| ***C08B 37/02*** | (2006.01) |

(52) U.S. Cl.

CPC ................ *A61K 8/73* (2013.01); *A61K 8/922* (2013.01); *A61Q 5/02* (2013.01); *A61Q 5/12* (2013.01); *C08B 37/0021* (2013.01); *A61K 2800/48* (2013.01); *A61K 2800/51* (2013.01); *A61K 2800/524* (2013.01); *A61K 2800/5426* (2013.01); *A61K 2800/596* (2013.01)

(58) Field of Classification Search

CPC ...... A61K 8/73; A61K 8/922; A61K 2800/48; A61K 2800/51; A61K 2800/524; A61K 2800/5426; A61K 2800/596; A61K 8/585; A61K 8/92; A61Q 5/02; A61Q 5/12; C08B 37/0021

See application file for complete search history.

(56) References Cited

U.S. PATENT DOCUMENTS

| | | | | |
|---|---|---|---|---|
| 4,411,891 | A | 10/1983 | Mizutani et al. | |
| 8,518,387 | B2 | 8/2013 | Drovetskaya et al. | |
| 2008/0003192 | A1 | 1/2008 | Modi | |
| 2009/0142283 | A1 * | 6/2009 | O'Brien | A61K 8/64 8/405 |
| 2010/0093584 | A1 * | 4/2010 | Brand | A61K 8/736 510/159 |
| 2010/0247472 | A1 | 9/2010 | Sau | |
| 2011/0177017 | A1 | 7/2011 | Coffindaffer et al. | |
| 2011/0213139 | A1 * | 9/2011 | Chan | A61Q 5/02 435/101 |
| 2012/0021025 | A1 | 1/2012 | Bendejacq et al. | |
| 2015/0098920 | A1 | 4/2015 | Stella et al. | |
| 2015/0203598 | A1 | 7/2015 | Landschutze et al. | |
| 2016/0287499 | A1 * | 10/2016 | Pimenta | A61K 8/608 |
| 2018/0237816 | A1 * | 8/2018 | Paullin | C08B 37/0021 |
| 2020/0323758 | A1 | 10/2020 | Karagianni et al. | |
| 2021/0071217 | A1 | 3/2021 | Paullin et al. | |

FOREIGN PATENT DOCUMENTS

| | | | |
|---|---|---|---|
| JP | 2000159642 | A * | 6/2000 |
| JP | 2000319139 | A | 11/2000 |
| JP | 4712222 | B2 | 6/2011 |

OTHER PUBLICATIONS

JP_2000159642_A + Figures—machine translation. "Shampooing Composition" 2000 (Year: 2000).*

Ethan. Dandruff Deconstructed. "What is in your Shampoo?" 2016 (Year: 2016).*

Heinze. "Functional Polymers Based on Dextran" Adv Polym Sci (2006) 205: 199-291. (Year: 2006).*

Ethan. "What is in your shampoo?" Dandruff Deconstructed (2016). (Year: 2016).*

JP2000159642A; machine translation provided. Umezawa 'Shampooing Composition' 2000. (Year: 2000).*

* cited by examiner

*Primary Examiner* — Ali Soroush
*Assistant Examiner* — Rajan Pragani
(74) *Attorney, Agent, or Firm* — CANTOR COLBURN LLP

(57) ABSTRACT

A hair care formulation is provided, comprising: a dermatologically acceptable vehicle; a dermatologically acceptable oil; and a deposition aid polymer, wherein the deposition aid polymer is a dextran polymer functionalized with an amine group; wherein the dextran polymer has a weight average molecular weight of 100,000 to 650,000 Daltons; and wherein the deposition aid polymer enhances deposition of the dermatologically acceptable oil from the hair care formulation onto mammalian hair.

9 Claims, No Drawings

HAIR OIL FORMULATION

The present invention relates to a hair care formulation. In particular, the present invention relates to a hair care formulation containing: a dermatologically acceptable vehicle; a dermatologically acceptable oil; and a deposition aid polymer, wherein the deposition aid polymer is a dextran polymer functionalized with an amine group; wherein the dextran polymer has a weight average molecular weight of 100,000 to 650,000 Daltons; and wherein the deposition aid polymer enhances deposition of the dermatologically acceptable oil from the hair care formulation onto mammalian hair.

Deposition of oil is of particular interest for various personal care compositions. In particular, there is interest for hair cleansers (e.g., shampoo, shampoo conditioners) that provide moisturizing/conditioning benefits in addition to cleaning benefits.

Hair cleansing has become an ubiquitous component of personal hygiene. Cleansing of the hair facilitates the removal of dirt, germs and other things that are perceived as harmful to the hair or the individual. Cleansing formulations typically including a surfactant to promote the removal of materials deposited on the hair. Unfortunately, the cleansing formulations remove both undesirable and desirable materials from hair. For example, cleansing formulations frequently undesirably remove oils from hair, which oils operate to protect hair from loss of moisture. Removal of too much oil from hair may leave the hair vulnerable to becoming dry and damaged. One solution to this concern is the selection of mild surfactants. Another approach is to incorporate additives that help replace the oils removed through deposition; however, this approach has proven difficult in implementation, particularly in rinse off applications.

In U.S. Pat. No. 7,067,499, Erazo-Majewicz, et al disclose personal care and household care product composition comprising at least one cationic polygalactomannan or a derivative of cationic polygalactomannans wherein the derivative moiety on the cationic derivatized polygalactomannan is selected from the group consisting of alkyl, hydroxyalkyl, alkylhydroxyalkyl, and carboxymethyl wherein the alkyl has a carbon chain containing from 1 to 22 carbons and the hydroxyalkyl is selected from the group consisting of hydroxyethyl, hydroxypropyl, and hydroxybutyl, wherein the at least one cationic polygalactomannan or derivative of cationic polygalactomannans have a mean average molecular weight (Mw) having a lower limit of 5,000 and an upper limit of 200,000 and having a light transmittance in a 10% aqueous solution of greater than 80% at a light wavelength of 600 nm and a protein content of less than 1.0% by weight of polysaccharide, and aldehyde functionality content of at least 0.01 meg/gram.

While conventionally used deposition aids such as soluble cationic modified celluloses (e.g., polyquaternium-10), guar hydroxypropyltrimonium chloride and other cationic polymers (e.g., polyquaternium-6, polyquaternium-7) provide a certain level of deposition in personal care cleansers; they nevertheless exhibit low efficiency necessitating a relatively high incorporation of the active into the personal care cleanser formulation to facilitate desired results. Such high active (e.g., oil) levels, however, detrimentally effect the foam/lathery in use consumer feel of the formulation and cost.

Accordingly, there remains a need for deposition aids that facilitate enhanced efficiency of oil deposition from hair care formulations.

The present invention provides a hair care formulation, comprising: a dermatologically acceptable vehicle; a dermatologically acceptable oil; and a deposition aid polymer, wherein the deposition aid polymer is a dextran polymer functionalized with an amine group; wherein the dextran polymer has a weight average molecular weight of 100,000 to 650,000 Daltons; and wherein the deposition aid polymer enhances deposition of the dermatologically acceptable oil from the cleansing formulation onto mammalian hair.

The present invention provides a method of depositing oil on to mammalian hair, comprising: selecting a hair care formulation of the present invention; and applying the hair care formulation to mammalian hair.

DETAILED DESCRIPTION

We have surprisingly found that oil deposition from hair care formulations can be enhanced through incorporation of a deposition aid polymer, wherein the deposition aid polymer is a dextran polymer functionalized with an amine group; wherein the dextran polymer has a weight average molecular weight of 100,000 to 650,000 Daltons; and wherein the deposition aid polymer enhances deposition of the oil from the cleansing formulation onto mammalian hair.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and conventional standards, such as polyethylene glycol standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons, or equivalently, g/mol.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the hair care formulation of the present invention is selected from the group consisting of a shampoo, a conditioning shampoo, a leave on hair conditioner, a rinse off hair conditioner, a hair coloring agent, a hair styling gel a heat protection spray. More preferably, the hair care formulation of the present invention is selected from the group consisting of a shampoo, a conditioning shampoo, a leave on hair conditioner and a rinse off hair conditioner. Still more preferably, the hair care formulation of the present invention is a shampoo, a conditioner or a conditioning shampoo. Most preferably, the hair care formulation of the present invention is a shampoo or a conditioning shampoo.

Preferably, the hair care formulation of the present invention, comprises: a dermatologically acceptable vehicle (preferably, wherein the hair care formulation comprises 25 to 99 wt % (preferably, 30 to 95 wt %; more preferably, 40 to 90 wt %; most preferably, 70 to 85 wt %), based on weight of the hair care formulation, of a dermatologically acceptable vehicle); a dermatologically acceptable oil (preferably, wherein the hair care formulation comprises 0.01 to 10 wt % (more preferably, 0.1 to 7.5 wt %; still more preferably, 1 to 6 wt %; most preferably, 2 to 5 wt %), based on weight of the hair care formulation, of the dermatologically acceptable oil); and a deposition aid polymer (preferably, wherein the hair care formulation comprises 0.05 to 1 wt % (preferably, 0.1 to 0.75 wt %; more preferably, 0.2 to 0.5 wt %; most preferably, 0.25 to 0.4 wt %), based on weight of the hair care formulation, of the deposition aid polymer), wherein the deposition aid polymer is a dextran polymer functionalized with an amine group; wherein the dextran polymer has a weight average molecular weight of 100,000 to 650,000 Daltons (preferably, 125,000 to 600,000 Daltons; more preferably, 130,000 to 575,000 Daltons; most preferably, 145,000 to 525,000 Daltons); and wherein the deposition aid polymer enhances deposition of the dermatologically acceptable oil from the cleansing formulation onto mammalian hair.

Preferably, the hair care formulation of the present invention is a liquid formulation. More preferably, the hair care formulation of the present invention is an aqueous liquid formulation.

Preferably, the hair care formulation of the present invention, comprises a dermatologically acceptable vehicle. More preferably, the hair care formulation of the present invention, comprises: 25 to 99 wt % (preferably, 30 to 97.5 wt %; more preferably, 60 to 95 wt %; most preferably, 75 to 90 wt %), based on weight of the hair care formulation, of a dermatologically acceptable vehicle. Still more preferably, the hair care formulation of the present invention, comprises: 25 to 99 wt % (preferably, 30 to 97.5 wt %; more preferably, 60 to 95 wt %; most preferably, 75 to 90 wt %), based on weight of the hair care formulation, of a dermatologically acceptable vehicle; wherein the dermatologically acceptable vehicle comprises water. Yet more preferably, the hair care formulation of the present invention, comprises: 25 to 99 wt % (preferably, 30 to 97.5 wt %; more preferably, 60 to 95 wt %; most preferably, 75 to 90 wt %), based on weight of the hair care formulation, of a dermatologically acceptable vehicle; wherein the dermatologically acceptable vehicle is selected from the group consisting of water and an aqueous $C_{1-4}$ alcohol mixture. Most preferably, the hair care formulation of the present invention, comprises: 25 to 99 wt % (preferably, 30 to 97.5 wt %; more preferably, 60 to 95 wt %; most preferably, 75 to 90 wt %), based on weight of the hair care formulation, of a dermatologically acceptable vehicle; wherein the dermatologically acceptable vehicle is water.

Preferably, the water used in the hair care formulation of the present invention is at least one of distilled water and deionized water. More preferably, the water used in the hair care formulation of the present invention is distilled and deionized.

Preferably, the hair care formulation of the present invention, comprises: a dermatologically acceptable oil. More preferably, the hair care formulation of the present invention, comprises: 0.01 to 10 wt % (preferably, 0.1 to 7.5 wt %; more preferably, 1 to 6 wt %; most preferably, 2 to 5 wt %), based on weight of the hair care formulation, of a dermatologically acceptable oil. Yet more preferably, the hair care formulation of the present invention, comprises: 0.01 to 10 wt % (preferably, 0.1 to 7.5 wt %; more preferably, 1 to 6 wt %; most preferably, 2 to 5 wt %), based on weight of the hair care formulation, of a dermatologically acceptable oil; wherein the dermatologically acceptable oil is selected from the group consisting of hydrocarbon oils (e.g., mineral oil, petroleum jelly, polyisobutene, hydrogenated polyisobutene, hydrogenated polydecene, polyisohexadecane; natural oils (e.g., caprylic and capric triglyceride, sunflower oil, soybean oil, coconut oil, argan oil, olive oil, almond oil); fragrance oils (e.g., limonene) and mixtures thereof. Still more preferably, the hair care formulation of the present invention, comprises: 0.01 to 10 wt % (preferably, 0.1 to 7.5 wt %; more preferably, 1 to 6 wt %; most preferably, 2 to 5 wt %), based on weight of the hair care formulation, of a dermatologically acceptable oil; wherein the dermatologically acceptable oil includes at least one of mineral oil, sunflower oil and coconut oil. Most preferably, the hair care formulation of the present invention, comprises: 0.01 to 10 wt % (preferably, 0.1 to 7.5 wt %; more preferably, 1 to 6 wt %; most preferably, 2 to 5 wt %), based on weight of the hair care formulation, of a dermatologically acceptable oil; wherein the dermatologically acceptable oil is coconut oil.

Preferably, the hair care formulation of the present invention comprises a deposition aid polymer, wherein the deposition aid polymer is a dextran polymer functionalized with an amine group; wherein the deposition aid polymer enhances deposition of a dermatologically acceptable oil from the hair care formulation onto mammalian hair. More preferably, the hair care formulation of the present invention comprises 0.05 to 1 wt % (preferably, 0.1 to 0.75 wt %; more preferably, 0.2 to 0.5 wt %; most preferably, 0.25 to 0.4 wt %), based on weight of the hair care formulation, of a deposition aid polymer; wherein the deposition aid polymer is a dextran polymer functionalized with an amine group; wherein the deposition aid polymer enhances deposition of a dermatologically acceptable oil from the hair care formulation onto mammalian hair. Most preferably, the hair care formulation of the present invention comprises 0.05 to 1 wt % (preferably, 0.1 to 0.75 wt %; more preferably, 0.2 to 0.5 wt %; most preferably, 0.25 to 0.4 wt %), based on weight of the hair care formulation, of a deposition aid polymer; wherein the deposition aid polymer is a dextran polymer functionalized with an amine group; wherein the deposition aid polymer has a Kjeldahl nitrogen content corrected for ash and volatiles, TKN, of 0.5 to 4.5 wt % (preferably, 0.75 to 4.0 wt %; more preferably, 0.9 to 3.75 wt %; most preferably, 1 to 3.5 wt %) (measured using a Buchi Kjel-Master K-375 automated analyzer, corrected for volatiles and ash measured as described in ASTM method D-2364); and wherein the deposition aid polymer enhances deposition of the dermatologically acceptable oil from the hair care formulation onto mammalian hair.

Preferably, the deposition aid polymer is a dextran polymer functionalized with an amine group. More preferably, the deposition aid polymer is a dextran polymer functionalized with an amine group; wherein the dextran polymer is a branched chain dextran polymer. Still more preferably, the deposition aid polymer is a dextran polymer functionalized with an amine group; wherein the dextran polymer comprises a branched chain dextran polymer; wherein the branched chain dextran polymer comprises a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages. Most preferably, the deposition aid polymer is a dextran polymer functionalized with an amine group; wherein the dextran polymer is a branched chain dextran polymer; wherein the branched chain dextran polymer comprises a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages according to formula (i)

(i)

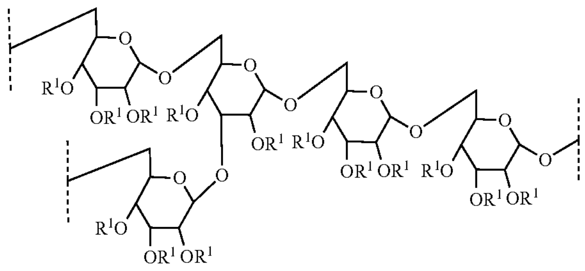

wherein $R^1$ is selected from a hydrogen, a $C_{1-4}$ alkyl group and a hydroxy $C_{1-4}$ alkyl group; and wherein the average branch off the dextran polymer backbone is <3 anhydroglucose units.

Preferably, the dextran polymer contain less than 0.01 wt %, based on weight of the dextran polymer, of alternan. More preferably, the dextran polymer contain less than 0.001 wt %, based on weight of the dextran polymer, of alternan. Most preferably, the dextran polymer contain less than the detectable limit of alternan.

Preferably, the deposition aid polymer is a dextran polymer functionalized with an amine group. More preferably, the deposition aid polymer is a dextran polymer functionalized with an amine group; wherein the amine group is selected from the group consisting of a tertiary amine group, a quaternary amine group and a combination thereof; wherein the deposition aid polymer enhances deposition of a dermatologically acceptable oil from the hair care formulation onto mammalian hair. Still more preferably, the deposition aid polymer is a dextran polymer functionalized with an amine group; wherein the amine group is selected from the group consisting of (a) a tertiary amine group and (b) a combination of a tertiary amine group and a quaternary amine group; wherein the deposition aid polymer enhances deposition of a dermatologically acceptable oil from the hair care formulation onto mammalian hair. Most preferably, the deposition aid polymer is a dextran polymer functionalized with an amine group; wherein the amine group is a tertiary amine group; wherein the deposition aid polymer enhances deposition of a dermatologically acceptable oil from the hair care formulation onto mammalian hair.

Preferably, the tertiary amine group is selected from the group consisting of trialkyl ammonium moieties of formula (A) bound to a pendent oxygen on the branched chain dextran polymer (A)

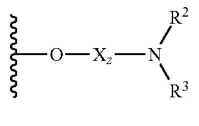

wherein

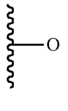

is a pendant oxygen on the branched chain dextran polymer; wherein X is a divalent linking group bonding the trialkyl ammonium moiety to the pendent oxygen on the branched chain dextran polymer (preferably, wherein X is selected from divalent hydrocarbon groups, which may optionally be substituted (e.g., with a hydroxy group, an alkoxy group, an ether group, a cationic nitrogen group); more preferably, wherein X is a $—(CH_2)_y—$ group, wherein y is 1 to 4 (preferably, 1 to 3; more preferably, 1 to 2; most preferably, 2); most preferably, X is a $—CH_2CH_2—$ group); wherein z is 0 or 1; wherein $R^2$ and $R^3$ are independently selected from the group consisting of a $C_{1-7}$ alkyl group (preferably, a $C_{1-3}$ alkyl group; more preferably, a methyl group and an ethyl group; most preferably, an ethyl group) or $R^2$ and $R^3$ may form a saturated or unsaturated ring structure (preferably, wherein the saturated or unsaturated ring structure including the N from which $R^2$ and $R^3$ are bound is selected from the group consisting of piperidine, piperazine, imidazole and morpholine; more preferably, wherein the saturated or unsaturated ring structure including the N from which $R^2$ and $R^3$ are bound is selected from the group consisting of imidazole and morpholine).

Preferably, the quaternary ammonium group is selected from the group consisting of at least one of (a) a dextran crosslinking group of formula (B)

(B)

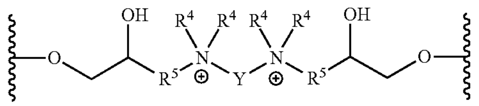

and (b) a quaternary ammonium group of formula (C)

(C)

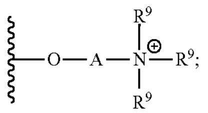

wherein

is a pendant oxygen on the dextran polymer; wherein each $R^4$ is independently selected from a substituted or unsubstituted $C_{1-6}$ alkyl group (wherein "substituted" means that the group in question contains at least one of a halogen, a hydroxy group, an amino group or a carboxy group) (preferably, wherein each $R^4$ is independently selected from an unsubstituted $C_{1-6}$ alkyl group; more preferably, wherein each $R^4$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^4$ is independently selected from the group consisting of a methyl group, an ethyl group, a propyl group, an isopropyl group, a butyl group, an isobutyl group, a tert-butyl group and a sec-butyl group; yet more preferably, wherein each $R^4$ is independently selected from the group consisting of a methyl group, an ethyl group, a propyl group and an isopropyl group; yet still more preferably, wherein each $R^4$ is independently selected from the group consisting of a methyl group and an ethyl group; most preferably, wherein each $R^4$ is a methyl group); wherein each $R^5$ is independently selected from the group consisting of a $C_{1-6}$ alkanediyl group (preferably, wherein each $R^5$ is independently selected from the group consisting of a $C_{1-4}$ alkanediyl group; more preferably, wherein each $R^5$ is independently selected from the group consisting of a $C_{1-2}$ alkanediyl group; most preferably, wherein each $R^5$ is a —$CH_2$— group); wherein Y is a divalent bridging group (preferably, wherein Y is a divalent bridging group selected from the group consisting of a $C_{1-6}$ alkanediyl group and a —$R^6$—O—$R^7$— group; more preferably, wherein Y is a —$R^6$—O—$R^7$— group); wherein $R^6$ and $R^7$ are independently selected from the group consisting of a $C_{1-6}$ alkanediyl group (preferably, wherein $R^6$ and $R^7$ are independently selected from the group consisting of a $C_{1-4}$ alkanediyl group; more preferably, wherein $R^6$ and $R^7$ are independently selected from the group consisting of a $C_{1-3}$ alkanediyl group; most preferably, wherein $R^6$ and $R^7$ are both a —$CH_2CH_2$— group)(preferably, wherein $R^6$ and $R^7$ are the same); wherein A is a divalent linking group bonding the quaternary ammonium moiety to the pendent oxygen on the dextran polymer (preferably, wherein A is selected from divalent hydrocarbon groups, which may optionally be substituted (e.g., with a hydroxy group, an alkoxy group, an ether group); more preferably, wherein A is a —$CH_2CH(OR^9)CH_2$— group, wherein $R^9$ is selected from the group consisting of a hydrogen and a $C_{1-4}$ alkyl group; most preferably, wherein A is a —$CH_2CH(OH)CH_2$— group); and wherein each $R^8$ is independently selected from the group consisting of a $C_{1-22}$ alkyl group (preferably, wherein each $R^8$ is independently selected from the group consisting of a $C_{1-3}$ alkyl group and a $C_{6-22}$ alkyl group; more preferably, wherein each $R^8$ is independently selected from the group consisting of a methyl group and an ethyl group; most preferably, wherein each $R^8$ is a methyl group). More preferably, the quaternary ammonium group is selected from the group consisting of at least one of (a) a dextran crosslinking group of formula (B) and (b) a quaternary ammonium group of formula (C); wherein the dextran crosslinking group of formula (B) is of Formula (D)

(D)

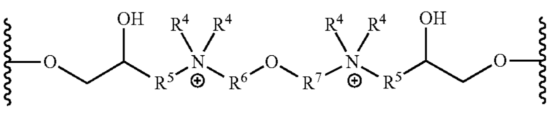

and wherein the quaternary ammonium group of formula (C) is of formula (E)

(E)

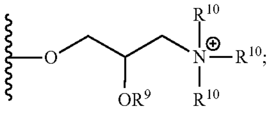

wherein

is a pendant oxygen on the dextran polymer; wherein each $R^4$ is independently selected from a substituted or unsubstituted $C_{1-6}$ alkyl group (preferably, wherein each $R^4$ is independently selected from an unsubstituted $C_{1-6}$ alkyl group; more preferably, wherein each $R^4$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^4$ is independently selected from the group consisting of a methyl group, an ethyl group, a propyl group, an isopropyl group, a butyl group, an isobutyl group, a tert-butyl group and a sec-butyl group; yet more preferably, wherein each $R^4$ is independently selected from the group consisting of a methyl group, an ethyl group, a propyl group and an isopropyl group; yet still more preferably, wherein each $R^4$ is independently selected from the group consisting of a methyl group and an ethyl group; most preferably, wherein each $R^4$ is a methyl group); wherein each $R^5$ is independently selected from the group consisting of a $C_{1-6}$ alkanediyl group (preferably, wherein each $R^5$ is a $C_{1-4}$ alkanediyl group; more preferably, wherein each $R^5$ is a $C_{1-2}$ alkanediyl group; most preferably, wherein each $R^5$ is a —$CH_2$— group); wherein $R^6$ and $R^7$ are independently selected from the group consisting of a $C_{1-6}$ alkanediyl group (preferably, wherein $R^6$ and $R^7$ are independently selected from the group consisting of a $C_{1-4}$ alkanediyl group; more preferably, wherein $R^6$ and $R^7$ are independently selected from the group consisting of a $C_{1-3}$ alkanediyl group; most preferably, a —$CH_2CH_2$— group)(preferably, wherein $R^6$ and $R^7$ are the same); wherein each $R^9$ is selected from the group consisting of a hydrogen and a $C_{1-4}$ alkyl group (preferably, wherein $R^9$ is a hydrogen); and wherein each R'° is independently selected from the group consisting of a methyl group and an ethyl group (preferably, a methyl group). Still more preferably, the quaternary ammonium group is selected from the group consisting of at least one of (a) a dextran crosslinking group of formula (B) and (b) a quaternary ammonium group of formula (C); wherein the dextran crosslinking group of formula (B) is selected from the group consisting of

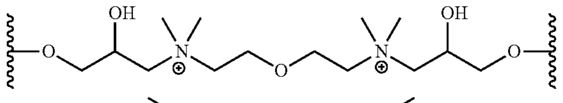
;

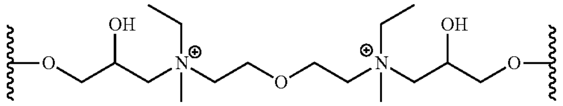
;

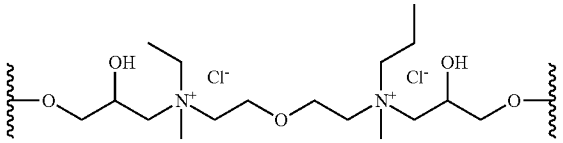
;

-continued

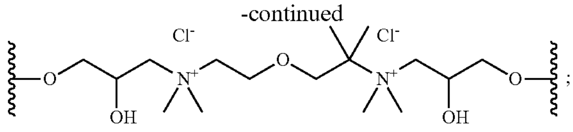

;

and mixtures thereof; and wherein the quaternary ammonium group of formula (C) is of formula (E); wherein

is a pendant oxygen on the dextran polymer; wherein each $R^9$ is selected from the group consisting of a hydrogen and a $C_{1-4}$ alkyl group (preferably, wherein $R^9$ is a hydrogen); and wherein each $R^{10}$ is independently selected from the group consisting of a methyl group and an ethyl group (preferably, a methyl group). Most preferably, the quaternary ammonium group is selected from the group consisting of (b) a quaternary ammonium group of formula (E); wherein

is a pendant oxygen on the dextran polymer; wherein each $R^9$ is selected from the group consisting of a hydrogen and a $C_{1-4}$ alkyl group (preferably, wherein $R^9$ is a hydrogen); and wherein each $R^{10}$ is independently selected from the group consisting of a methyl group and an ethyl group (preferably, a methyl group).

Preferably, the hair care formulation of the present invention comprises a deposition aid polymer, wherein the deposition aid polymer is a dextran polymer functionalized with an amine group; wherein the dextran polymer has a weight average molecular weight of 100,000 to 650,000 (preferably, 125,000 to 600,000; more preferably, 130,000 to 575,000; most preferably, 145,000 to 525,000) Daltons; and wherein the deposition aid polymer enhances deposition of the dermatologically acceptable oil from the hair care formulation onto mammalian hair. More preferably, the hair care formulation of the present invention comprises 0.05 to 1 wt % (preferably, 0.1 to 0.75 wt %; more preferably, 0.2 to 0.5 wt %; most preferably, 0.25 to 0.4 wt %), based on weight of the hair care formulation, of a deposition aid polymer, wherein the deposition aid polymer is a dextran polymer functionalized with an amine group; wherein the dextran polymer has a weight average molecular weight of 100,000 to 650,000 (preferably, 125,000 to 600,000; more preferably, 130,000 to 575,000; most preferably, 145,000 to 525,000) Daltons; and wherein the deposition aid polymer enhances deposition of the dermatologically acceptable oil from the hair care formulation onto mammalian hair. Most preferably, the hair care formulation of the present invention comprises 0.05 to 1 wt % (preferably, 0.1 to 0.75 wt %; more preferably, 0.2 to 0.5 wt %; most preferably, 0.25 to 0.4 wt %), based on weight of the hair care formulation, of a deposition aid polymer; wherein the deposition aid polymer is a dextran polymer functionalized with an amine group; wherein the dextran polymer has a weight average molecular weight of 100,000 to 650,000 (preferably, 125,000 to 600,000; more preferably, 130,000 to 575,000; most preferably, 145,000 to 525,000) Daltons; wherein the cationic dextran polymer has a Kjeldahl nitrogen content corrected for ash and volatiles, TKN, of 0.5 to 4.5 wt % (preferably, 0.75 to 4.0 wt %; more preferably, 0.9 to 3.75 wt %; most preferably, 1 to 3 wt %) (measured using a Buchi KjelMaster K-375 automated analyzer, corrected for volatiles and ash measured as described in ASTM method D-2364); and wherein the deposition aid polymer enhances deposition of the dermatologically acceptable oil from the hair care formulation onto mammalian hair.

Preferably, the deposition aid polymer comprises <0.001 meg/gram (preferably, <0.0001 meq/gram; more preferably, <0.00001 meq/gram; most preferably,<detectable limit) of aldehyde functionality.

Preferably, the deposition aid polymer comprises <0.1% (preferably, <0.01%; more preferably, <0.001%; most preferably,<detectable limit), of the linkages between individual glucose units in the deposition aid polymer are β-1,4 linkages.

Preferably, the deposition aid polymer comprises <0.1% (preferably, <0.01%; more preferably, <0.001%; most preferably,<detectable limit), of the linkages between individual glucose units in the deposition aid polymer are β-1,3 linkages.

Preferably, the deposition aid polymer comprises <0.001 meq/gram (preferably, <0.0001 meq/gram; more preferably, <0.00001 meq/gram; most preferably,<detectable limit) of silicone containing functionality.

Preferably, the deposition aid polymer comprises <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties. More preferably, the deposition aid polymer comprises <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties; wherein the reactive siloxane is a polymer which may comprise one or more functional moieties selected from the group consisting of amino, amido, alkoxy, hydroxy, polyether, carboxy, hydride, mercapto, sulfate phosphate, and/or quaternary ammonium moieties—these moieties may be attached directly to the siloxane backbone through a bivalent alkylene radical, (i.e., pendant) or may be part of the backbone.

Preferably, the hair care formulation of the present invention, optionally, further comprises at least one additional ingredient selected from the group consisting of a hair care cleansing surfactant; an antimicrobial agent/preservative (e.g., benzoic acid, sorbic acid, phenoxyethanol, methylisothiazolinone); a rheology modifier (e.g., PEG-150 pentaerythrityl tetrastearate); a soap; a colorant; pH adjusting agent; an antioxidant (e.g., butylated hydroxytoluene); a humectant (e.g., glycerin, sorbitol, monoglycerides, lecithins, glycolipids, fatty alcohols, fatty acids, polysaccharides, sorbitan esters, polysorbates (e.g., Polysorbate 20, Polysorbate 40, Polysorbate 60, and Polysorbate 80), diols (e.g., propylene glycol), diol analogs, triols, triol analogs, cationic polymeric polyols); a wax; a foaming agent; an emulsifying agent; a colorant; a fragrance; a chelating agent (e.g., tetrasodium ethylene diamine tetraacetic acid); a preservative (e.g., benzoic acid, sorbic acid, phenoxyethanol, methylisothiazolinone); a bleaching agent; a lubricating agent; a sensory modifier; a sunscreen additive; a vitamin; a protein/amino acid; a plant extract; a natural ingredient; a bioactive agent; an anti-aging agent; a pigment; an acid; a penetrant; an anti-static agent; an anti-frizz agent; an anti-dandruff agent; a hair waving/straightening agent; a hair styling agent; a hair oil; an absorbent; a hard particle; a soft particle; a conditioning agent (e.g., guar hydroxypropyltrimonium chloride, PQ-10, PQ-7); a slip agent; an opacifier; a pearlizing agent and a salt. More preferably, the hair care formulation of the present invention, optionally, further comprises at least one additional ingredient selected from the group consisting of a hair care cleansing surfactant; an antimicrobial agent/preservative (e.g., benzoic acid, sorbic acid, phenoxyethanol, methylisothiazolinone); a rheology modifier (e.g., PEG-150 pentaerythrityl tetrastearate); and a chelating agent (e.g., tetrasodium ethylene diamine tetraacetic acid). Most preferably, the hair care formulation of the present invention, optionally, further comprises at least one additional ingredient selected from the group consisting of a hair care cleansing surfactant; an antimicrobial agent/preservative mixture of phenoxyethanol and methylisothiazolinone; PEG-150 pentaerythrityl tetrastearate; tetrasodium ethylene diamine tetraacetic acid and a mixture of phenoxyethanol and methylisothiazolinone.

Preferably, the hair care formulation of the present invention further comprises a hair care cleaning surfactant. More preferably, the hair care formulation of the present invention further comprises a hair care cleansing surfactant, wherein the hair care cleansing surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium lauryl ether sulfate (SLES)), sulfonates (e.g., sodium $C_{14-16}$ olefin sulfonate), succinates (e.g., disodium lauryl sulfosuccinate), fatty alkanolamides (e.g., cocamide monoethanolamine, cocamide diethanolamine, soyamide diethanolamine, lauramide diethanolamine, oleamide monoisopropanolamine, stearamide monoethanolamine, myristamide monoethanolamine, lauramide monoethanolamine, capramide diethanolamine, ricinoleamide diethanolamine, myristamide diethanolamine, stearamide diethanolamine, oleylamide diethanolamine, tallowamide diethanolamine, lauramide monoisopropanolamine, tallowamide monoethanolamine, isostearamide diethanolamine, isostearamide monoethanolamine) and mixtures thereof. Still more preferably, the hair care formulation of the present invention further comprises a hair care cleaning surfactant; wherein the hair care formulation is selected from the group consisting of a shampoo and a conditioning shampoo; and wherein the hair care cleaning surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium lauryl ether sulfate (SLES)), sulfonates (e.g., sodium $C_{14-16}$ olefin sulfonate), succinates (e.g., disodium lauryl sulfosuccinate), fatty alkanolamides (e.g., cocamide monoethanolamine, cocamide diethanolamine, soyamide diethanolamine, lauramide diethanolamine, oleamide monoisopropanolamine, stearamide monoethanolamine, myristamide monoethanolamine, lauramide monoethanolamine, capramide diethanolamine, ricinoleamide diethanolamine, myristamide diethanolamine, stearamide diethanolamine, oleylamide diethanolamine, tallowamide diethanolamine, lauramide monoisopropanolamine, tallowamide monoethanolamine, isostearamide diethanolamine, isostearamide monoethanolamine) and mixtures thereof. Most preferably, the hair care formulation of the present invention further comprises a hair care cleaning surfactant; wherein the hair care formulation is selected from the group consisting of a shampoo and a conditioning shampoo; and wherein the hair care cleaning surfactant comprises a mixture of a betaine (preferably, cocamidopropyl betaine), a sulfate (preferably, sodium lauryl ether sulfate (SLES)), and a fatty alkanolamide (preferably, cocamide monoethanolamine).

Preferably, the hair care formulation of the present invention further comprises 0.01 to 80 wt % (more preferably, 1 to 50 wt %; still more preferably, 5 to 20 wt %, most preferably, 7 to 15 wt %), based on weight of the hair care formulation, of a hair care cleaning surfactant. More preferably, the hair care formulation of the present invention further comprises 0.01 to 80 wt % (more preferably, 1 to 50 wt %; still more preferably, 5 to 20 wt %, most preferably, 7 to 15 wt %), based on weight of the hair care formulation, of a hair care cleaning surfactant, wherein the hair care cleaning surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium lauryl ether sulfate (SLES)), sulfonates (e.g., sodium $C_{14-16}$ olefin sulfonate), succinates (e.g., disodium lauryl sulfosuccinate), fatty alkanolamides (e.g., cocamide monoethanolamine, cocamide diethanolamine, soyamide diethanolamine, lauramide diethanolamine, oleamide monoisopropanolamine, stearamide monoethanolamine, myristamide monoethanolamine, lauramide monoethanolamine, capramide diethanolamine, ricinoleamide diethanolamine, myristamide diethanolamine, stearamide diethanolamine, oleylamide diethanolamine, tallowamide diethanolamine, lauramide monoisopropanolamine, tallowamide monoethanolamine, isostearamide diethanolamine, isostearamide monoethanolamine) and mixtures thereof. Still more preferably, the hair care formulation of the present invention further comprises 0.01 to 80 wt % (more preferably, 1 to 50 wt %; still more preferably, 5 to 20 wt %, most preferably, 7 to 15 wt %), based on weight of the hair care formulation, of a hair care cleaning surfactant; wherein the hair care formulation is a body wash formulation and wherein the hair care cleaning surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium lauryl ether sulfate (SLES)), sulfonates (e.g., sodium $C_{14-16}$ olefin sulfonate), succinates (e.g., disodium lauryl sulfosuccinate), fatty alkanolamides (e.g., cocamide monoethanolamine, cocamide diethanolamine, soyamide diethanolamine, lauramide diethanolamine, oleamide monoisopropanolamine, stearamide monoethanolamine, myristamide monoethanolamine, lauramide monoethanolamine, capramide diethanolamine, ricinoleamide diethanolamine, myristamide diethanolamine, stearamide diethanolamine, oleylamide diethanolamine, tallowamide diethanolamine, lauramide monoisopropanolamine, tallowamide monoethanolamine, isostearamide diethanolamine, isostearamide monoethanolamine) and mixtures thereof. Most preferably, the hair care formulation of the present invention further comprises 0.01 to 80 wt % (more preferably, 1 to 50 wt %; still more preferably, 5 to 20 wt %, most preferably, 7 to 15 wt %), based on weight of the hair care formulation, of a hair care cleaning surfactant; wherein the hair care formulation is a body wash formulation and wherein the hair care cleaning surfactant comprises a mixture of a betaine (preferably, cocamidopropyl betaine), a sulfate (preferably, sodium lauryl ether sulfate (SLES)), and a fatty alkanolamide (preferably, cocamide monoethanolamine).

Preferably, the hair care formulation further comprises a thickener. More preferably, the hair care formulation further comprises a thickener, wherein the thickener is selected to increase the viscosity of the hair care formulation, preferably without substantially modifying the other properties of the hair care formulation. Preferably, the hair care formulation further comprises a thickener, wherein the thickener is selected to increase the viscosity of the hair care formulation, preferably without substantially modifying the other properties of the hair care formulation and wherein the thickener accounts for 0 to 5.0 wt % (preferably, 0.1 to 5.0 wt %; more preferably, 0.2 to 2.5 wt %; most preferably, 0.5 to 2.0 wt %), based on weight of the hair care formulation.

Preferably, the hair care formulation of the present invention further comprises an antimicrobial agent/preservative. More preferably, the hair care formulation of the present invention further comprises an antimicrobial/preservative, wherein the antimicrobial/preservative is selected from the group consisting of phenoxyethanol, benzoic acid, benzyl alcohol, sodium benzoate, DMDM hydantoin, 2-ethylhexyl glyceryl ether, isothiazolinone (e.g., methylchloroisothiazolinone, methylisothiazolinone) and mixtures thereof. Still more preferably, the hair care formulation of the present invention, further comprises an antimicrobial/preservative, wherein the antimicrobial/preservative is a mixture of phenoxyethanol and an isothiazolinone (more preferably, wherein the antimicrobial/preservative is a mixture of phenoxyethanol and methylisothiazolinone).

Preferably, the hair care formulation of the present invention optionally further comprises a pH adjusting agent. More preferably, the hair care formulation of the present invention, further comprises a pH adjusting agent, wherein the hair care formulation has a pH of 4 to 9 (preferably, 4.25 to 8; more preferably, 4.5 to 7; most preferably, 4.75 to 6).

Preferably, the pH adjusting agent is selected from the group consisting of at least one of citric acid, lactic acid, hydrochloric acid, aminoethyl propanediol, triethanolamine, monoethanolamine, sodium hydroxide, potassium hydroxide, amino-2-methyl-1-propanol. More preferably, the pH adjusting agent is selected from the group consisting of at least one of citric acid, lactic acid, sodium hydroxide, potassium hydroxide, triethanolamine, amino-2-methyl-1-propanol. Still more preferably, the pH adjusting agent includes citric acid. Most preferably, the pH adjusting agent is citric acid.

Preferably, the method of depositing oil on to mammalian hair of the present invention, comprises: selecting a hair care formulation of the present invention and applying the hair care formulation to mammalian hair. More preferably, the method of depositing oil on to mammalian hair of the present invention, further comprises: rinsing the hair care formulation from the mammalian hair with a rinse water. Most preferably, the method of depositing oil on to mammalian hair of the present invention, comprises: selecting a hair care formulation of the present invention; applying the hair care formulation to mammalian hair; and rinsing the hair care formulation from the mammalian hair; wherein the hair care formulation is at least one of a shampoo and a conditioner.

Some embodiments of the present invention will now be described in detail in the following Examples.

Example S1: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran polymer (30.38 g; Sigma-Aldrich product D4876) and deionized water (100.32 g). The weight average molecular weight of the dextran polymer was 100,000 to 200,000 Daltons. The addition funnel was charged with a 70% aqueous solution of 2,3-epoxypropyltrimethylammonium chloride (27.04 g; QUAB® 151 available from SKW QUAB Chemicals). The flask contents were allowed to stir until the dextran polymer dissolved in the deionized water. While the contents were stirring, the apparatus was purged with nitrogen to displace any oxygen entrained in the system. The nitrogen flow rate was about 1 bubble per second. The mixture was purged with nitrogen while stirring for one hour. Using a plastic syringe, a 25% aqueous sodium hydroxide solution (4.75 g) was added over a period of a few minutes to the flask contents with stirring under nitrogen. The flask contents were then allowed to stir under nitrogen for 30 minutes. The contents of the addition funnel were then charged to the flask contents dropwise over a few minutes under nitrogen with continued stirring. After the contents of the addition funnel were transferred to the flask contents, the mixture was allowed to stir for 5 minutes. Then heat was applied to the flask contents with a heating mantle controlled using the J-KEM controller set at 55° C. The flask contents were heated to and maintained at 55° C. for 90 minutes. The flask contents were then cooled to room temperature while maintaining a positive nitrogen pressure in the flask. When the flask contents reached room temperature, glacial acetic acid (2.5 g) was added. The polymer was recovered by non-solvent precipitation from methanol, recovering the precipitated polymer by vacuum filtration using a Buchner funnel and dried overnight in vacuo at 50° C. The product branched chain cationic dextran polymer was an off-white solid, with a volatiles content of 3.41%, an ash content of 0.03% (as sodium chloride). The volatiles and ash were measured as described in ASTM method D-2364. The Kjeldahl nitrogen content, TKN, was measured using a Buchi KjelMaster K-375 automated analyzer, and was found to be 1.67% (corrected for volatiles and ash), which corresponds to a trimethylammonium degree of substitution of 0.24.

Example S2: Synthesis of Tertiary Amine Functionalized Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran (30.27 g; Aldrich product #D4876), 2-chloro-N,N-diethylethylamine hydrochloride (19.39 g) and deionized water (140.58 g). The weight average molecular weight of the dextran was 100,000 to 200,000 Daltons. While the contents were stirring, the apparatus was purged with nitrogen to displace any oxygen entrained in the system. The nitrogen flow rate was about 1 bubble per second. The mixture was purged with nitrogen while stirring for one hour. Using a plastic syringe, a 50% aqueous sodium hydroxide solution (12.52 g) was added over a period of a few minutes to the flask contents with stirring under nitrogen. The flask contents were then allowed to stir under nitrogen for 5 minutes. Then heat was applied to the flask contents with a heating mantle controlled using the J-KEM controller set at 70° C. The flask contents were heated to and maintained at 70° C. for three hours. The flask contents were then cooled to room temperature while maintaining a positive nitrogen pressure in the flask. When the flask contents reached room temperature, the flask contents were neutralized by adding glacial acetic acid (10.0 g). An excess of methanol was then added to the flask contents with vigorous stirring to precipitate tertiary amine functionalized dextran polymer from solution. The precipitated tertiary amine functionalized dextran polymer was then recovered by filtration through a Buchner funnel and dried overnight in vacuo at 50° C. The product branched chain cationic dextran polymer was an off-white solid (30.60 g), with a volatiles content of 3.58%, an ash content of 0.01% (as sodium chloride). The volatiles and ash were measured as described in ASTM method D-2364. The Kjeldahl nitrogen content was measured using a Buchi KjelMaster K-375 automated analyzer, and was found to be 2.26% (corrected for volatiles and ash), which corresponds to a tertiary amine degree of substitution of 0.335.

Examples S3-S6: Synthesis of Cationic Dextran Polymer

Cationic dextran polymers were prepared substantially as described in Example S2 but varying the feeds to giving the properties noted in TABLE 1.

TABLE 1

| Example | Dextran | Linkages α-D-(1-6) | Linkages α (1-3) | Kjeldahl Nitrogen (wt %) | Molecular weight (Da) |
|---|---|---|---|---|---|
| S2 | D4876[a] | 95% | 5% | 2.26 | ~150,000 |
| S3 | D4876[a] | 95% | 5% | 1.188 | ~150,000 |
| S4 | D4876[a] | 95% | 5% | 3.25 | ~150,000 |
| S5 | D4876[a] | 95% | 5% | 3.575 | ~150,000 |
| S6 | Dextran powder[b] | — | — | 3.075 | ~500,000 |

[a]available from Sigma-Aldrich
[b]available from Dextran Products Limited

Example S7: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran polymer (30.4 g; Sigma-Aldrich product D4876) and deionized water (140 g). The weight average molecular weight of the dextran polymer was 100,000 to 200,000 Daltons. The addition funnel was charged with a 70% aqueous solution of 2,3-epoxypropyltrimethylammonium chloride (27.1 g; QUAB® 151 available from SKW QUAB Chemicals). The flask contents were allowed to stir until the dextran polymer dissolved in the deionized water. While the contents were stirring, the apparatus was purged with nitrogen to displace any oxygen entrained in the system. The nitrogen flow rate was about 1 bubble per second. The mixture was purged with nitrogen while stirring for one hour. Using a plastic syringe, a 25% aqueous sodium hydroxide solution (4.75 g) was added over a period of a few minutes to the flask contents with stirring under nitrogen. The flask contents were then allowed to stir under nitrogen for 30 minutes. The contents of the addition funnel were then charged to the flask contents dropwise over a few minutes under nitrogen with continued stirring. After the contents of the addition funnel were transferred to the flask contents, the mixture was allowed to stir for 5 minutes. Then heat was applied to the flask contents with a heating mantle controlled using the J-KEM controller set at 55° C. The flask contents were heated to and maintained at 55° C. for 90 minutes. The flask contents were then cooled to room temperature while maintaining a positive nitrogen pressure in the flask. When the flask contents reached room temperature, glacial acetic acid (2.5 g) was added. The polymer was recovered by non-solvent precipitation from methanol, recovering the precipitated polymer by vacuum filtration using a Buchner funnel and dried overnight in vacuo at 50° C. The product branched chain cationic dextran polymer was an off-white solid, with a volatiles content of 3.22%, an ash content of 1.38% (as sodium chloride). The volatiles and ash were measured as described in ASTM method D-2364. The Kjeldahl nitrogen content, TKN, was measured using a Buchi KjelMaster K-375 automated analyzer, and was found to be 1.52% (corrected for volatiles and ash), which corresponds to a trimethylammonium degree of substitution of 0.211.

Example SX: Synthesis of Crosslinking Agent

Bis[2-(N,N-dimethyamino)ethyl]ether (10.84 g) and water (23.12 g) were mixed together in a container. The pH of the container contents were pH adjusted to 8.5 with concentrated hydrochloric acid. The set point temperature for the container contents was maintained at 25° C. while 99.9% epichlorohydrin (20.84 g) was added to the container over a period of 60 minutes. The set point temperature of the container contents was maintained at 25° C. for an additional 2 hours, before raising the set point temperature to 50° C. and maintaining that temperature set point for 2 hours. The pH of the container contents was then lowered to <2.0 with concentrated hydrochloric acid and the set point temperature was increased to 70° C. and maintaining that temperature set point for an hour. The container contents were then cooled. After the temperature of the container contents fell below 50° C., the pH of the container contents was adjusted to 4-6 with 50% sodium hydroxide solution. An extraction of the container contents was then performed with methylene chloride seven times (1 vol:1 vol), then the residual methylene chloride was removed conventionally. The recovered material contained 39.4 wt % product solids. The product solids were analyzed via $^{13}C$ NMR to confirm the product was

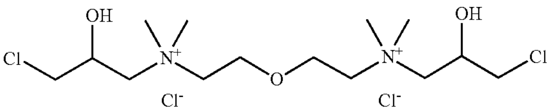 [SMILES: C[N+](C)(CCOCC[N+](C)(C)CC(O)CCl)CC(O)CCl ; [Cl-] ; [Cl-]]

N,N'-(oxybis(ethane-2,1-diyl))bisβ-chloro-2-hydroxy-N,N-dimethylpropan-1-aminium) chloride.

Example S8: Synthesis of Crosslinked Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran (23.23 g; Aldrich product #D4876) and deionized water (120 g). The weight average molecular weight of the dextran was 100,000 to 200,000 Daltons. While the contents were stirring, the apparatus was purged with nitrogen to displace any oxygen entrained in the system. The nitrogen flow rate was about 1 bubble per second. The mixture was purged with nitrogen while stirring for one hour. Using a plastic syringe, a 50% aqueous sodium hydroxide solution (14.9 g) was added over a period of a few minutes to the flask contents with stirring under nitrogen. The flask contents were then allowed to stir under nitrogen for 30 minutes. Then a 47% aqueous solution of a crosslinking agent prepared according to Example SX (74.45 g) was added to the flask contents and allowed to stir for five minutes prior to heating. Then heat was applied to the flask contents with a heating mantle controlled using the J-KEM controller set at 55° C. The flask contents were heated to and maintained at 55° C. for 90 minutes. The flask contents were then cooled to room temperature while maintaining a positive nitrogen pressure in the flask. When the flask contents reached room temperature, the flask contents were neutralized by adding glacial acetic acid (3.0 g) and the flask contents were allowed to stir for ten minutes. The flask contents were then diluted and transferred without purification for use; the diluted product solids content was 11.1 wt %. An aliquot of the solution was precipitated from methanol and dried in vacuo at 50° C. The total Kjeldahl nitrogen content, TKN, of the dried precipitate was measured using a Buchi KjelMaster K-375 automated analyzer at 2.72 wt %.

Comparative Examples CF1-CF2 and Examples F1-F8: Shampoo Formulations

A shampoo formulation was prepared in each of Comparative Examples CF1-CF2 and Examples F1-F8 using the generic shampoo formulation noted in TABLE 2.

TABLE 2

| Ingredient INCI name | CF1 wt % | CF2 wt % | F1 wt % | F2 wt % | F3 wt % | F4 wt % | F5 wt % | F6 wt % | F7 wt % | F8 wt % |
|---|---|---|---|---|---|---|---|---|---|---|
| Deionized water | q.s. 100 | | | | | | | | | |
| 30 wt % aq. soln. Sodium Lauryl Ether Sulfate[1] | 30 | 30 | 30 | 30 | 30 | 30 | 30 | 30 | 30 | 30 |
| Guar hydroxypropyltrimonium chloride[2] | — | 0.3 | | — | — | — | — | — | — | — |
| Example S1 | — | — | 0.3 | — | — | — | — | — | — | — |
| Example S2 | — | — | — | 0.3 | — | — | — | — | — | — |
| Example S3 | — | — | — | — | 0.3 | — | — | — | — | — |
| Example S4 | — | — | — | — | — | 0.3 | — | — | — | — |
| Example S5 | — | — | — | — | — | — | 0.3 | | — | — |
| Example S6 | — | — | — | — | — | — | — | 0.3 | — | — |
| Example S7 | — | — | — | — | — | — | — | — | 0.3 | — |
| Example S8 | — | — | — | — | — | — | — | — | — | 0.3 |
| Tetrasodium EDTA[3] | 0.2 | 0.2 | 0.2 | 0.2 | 0.2 | 0.2 | 0.2 | 0.2 | 0.2 | 0.2 |
| 45 wt % aq. soln. PEG-150 Pentaerythrityl Tetrastearate[4] | 1.0 | 1.0 | 1.0 | 1.0 | 1.0 | 1.0 | 1.0 | 1.0 | 1.0 | 1.0 |
| Cocamide MEA[5] | 1.0 | 1.0 | 1.0 | 1.0 | 1.0 | 1.0 | 1.0 | 1.0 | 1.0 | 1.0 |
| 30 wt % aq. soln. Cocamidopropyl Betaine[6] | 6.0 | 6.0 | 6.0 | 6.0 | 6.0 | 6.0 | 6.0 | 6.0 | 6.0 | 6.0 |
| Phenoxyethanol and Methylisothiazolinone[7] | 0.5 | 0.5 | 0.5 | 0.5 | 0.5 | 0.5 | 0.5 | 0.5 | 0.5 | 0.5 |
| Coconut oil[8] | 4.0 | 4.0 | 4.0 | 4.0 | 4.0 | 4.0 | 4.0 | 4.0 | 4.0 | 4.0 |

[1]available from Stepan Company under tradename Steol ® CS-330
[2]available from Solvay Novecare under tradename Jaguar Excel
[3]available from The Dow Chemical Company under tradename Versene ™ 220
[4]available from Croda Inc. under tradename Crothix-PA-(MH)
[5]available from Croda Inc. under tradename Incromide CMEA
[6]available from Stepan Company under tradename Amphosol CA
[7]available from The Dow Chemical Company under tradename Neolone ™ PE
[8]available from Marico Parachute brand

Comparative Examples C1-C2 and Examples 1-6: Coconut Oil Deposition Analysis The coconut oil deposition on hair from the shampoo formulations prepared according to Comparative Examples C1-C2 and Examples 1-6 was quantified using GC-MS.

Hair tresses (2 g, European Virgin Brown available from International Hair Importers) were initially washed in a 9 wt % sodium laureth sulfate (SLES) solution and rinsed with water flowing at 0.4 L/min for 30 seconds. Following the initial wash step, the hair tresses were then washed with a shampoo formulation of Comparative Examples C1-C2 and Example 1-6 by applying 0.8 g of the shampoo formulation to the hair tress and massaging in for 30 seconds on each side and then rinsing with water flowing at 0.4 L/min for 15 seconds on each side.

The treated hair samples were extracted with hexanes on a shaker overnight (~12 hours). A 1 M KOH in methanol solution was prepared. An extract from each hair sample (4 mL) was mixed in a vial with 1 M KOH (0.4 mL) and octadecane (0.2 mL, 100 ppm). The vials were then placed on a shaker for 1 hour. The vials were then placed in a hood for 5 minutes. A 3 mL sample from the top layer in each vial was mixed with 3 mL of saturated aqueous NaCl solution in a separate vial, which was then placed on a shaker for 5 minutes. The vials were then allowed to settle for 5 minutes before taking a 1 mL sample from the top layer and injecting into a GC-MS for analysis. The instrument parameters used are provided in TABLE 3.

TABLE 3

| | |
|---|---|
| Instrument | Agilent 7890A GC/5977A MS |
| Data system | Masshunter |
| Column: | Agilent DB-WAx, 30 m × 0.25 mm, 0.25 μm film |
| Carrier flow rate | 1.2 mL/min Helium<br>column connected to a split plate<br>restrictor capillary (5.0 m × 0.180 mm × 0 μm) |
| Inlet | Temperature: 250° C.<br>Injection 1 μL<br>Split ratio: 10:1 |
| Oven Temperature Programming: | 100° C. for 2 min, ramped at 10° C./min to 250° C., and held for 5 min. |
| MS transfer line temperature | 250° C. |
| SIM Parameters: | Group 1: 5-11 min; octadecane (as an internal standard): $t_R$, 9.93 min; ion 57 (quantifier) and 71 (qualifier)<br>Group 2: 11 min; $C_{14}$ acid methyl ester: $t_R$, 12.15 min; ion 74 (quantifier) and 87 (qualifier) |

The results are provided in TABLE 4.

TABLE 4

| Example | Shampoo Formulation | TKN % | Coconut oil deposition (wt %) |
|---|---|---|---|
| C1 | Comparative Example CF1 | — | 0.30 |
| C2 | Comparative Example CF2 | 1.67 | 1.80 |
| 1 | Example F1 | 1.67 | 1.20 |
| 2 | Example F2 | 2.26 | 4.30 |
| 3 | Example F3 | 1.19 | 0.90 |
| 4 | Example F4 | 3.25 | 1.90 |
| 5 | Example F5 | 3.58 | 1.50 |
| 6 | Example F6 | 3.08 | 2.50 |

Comparative Examples C3-C4 and Examples 7-8: Coconut Oil Deposition Analysis

The coconut oil deposition on hair from the shampoo formulations prepared according to Comparative Examples C3-C4 and Examples 7-8 was quantified using GC-MS.

Hair tresses (2 g, European Virgin Brown available from International Hair Importers) were initially washed in a 9 wt % sodium laureth sulfate (SLES) solution and rinsed with water flowing at 0.4 L/min for 30 seconds. Following the initial wash step, the hair tresses were then washed with a shampoo formulation of Comparative Examples C3-C4 and Example 7-8 by applying 0.8 g of the shampoo formulation to the hair tress and massaging in for 30 seconds on each side and then rinsing with water flowing at 0.4 L/min for 15 seconds on each side.

The treated hair samples were extracted with hexanes on a shaker overnight (~12 hours). A 1 M KOH in methanol solution was prepared. An extract from each hair sample (4 mL) was mixed in a vial with 1 M KOH (0.4 mL). The vials were then placed on a shaker for 1 hour. The vials were then placed in a hood for thirty (30) minutes to settle. The hexane layer in the vials was then filtered into an autosampler vial using a 0.2 μm PTFE filter. The sample solution was further diluted 10 times in hexane and shaken for 5 minutes and then allowed to settle for 5 minutes before taking a 1 mL sample from the top layer and injecting into a GC-MS for analysis. The instrument parameters used are provided in TABLE 5.

TABLE 5

| | |
|---|---|
| Instrument | Agilent 7890B GC/5977A MSD |
| Column: | Agilent DB-WAxUI, 30 m × 0.25 mm, 0.25 um film |
| Carrier flow rate | 1 mL/min Helium |
| Inlet | Temperature: 250° C.<br>Injection 1 μL<br>Split ratio: 10:1 |
| MS Detector | Transfer line temperature: 250° C.<br>MS Ion source (EI) Temperature: 230° C.<br>MS Quad temperature: 150° C.<br>EMVolts: 2135 V<br>Energy: 70 eV<br>Emission: 35 μA<br>Gain factor: 0.65<br>MS scan: m/z 40-400 (identification and confirmation)<br>SIM ions: m/z 74 (quantification) |

The results are provided in TABLE 6.

| Example | Shampoo Formulation | TKN % | Coconut oil deposition (wt %) |
|---|---|---|---|
| C3 | Comparative Example CF1 | — | 0.20 |
| C4 | Comparative Example CF2 | 1.67 | 2.50 |
| 7 | Example F7 | 1.52 | 2.60 |
| 8 | Example F8 | 2.27 | 3.00 |

We claim:

1. A hair care formulation, comprising:

a dermatologically acceptable vehicle;

a dermatologically acceptable oil; and a deposition aid polymer, wherein the deposition aid polymer is a dextran polymer functionalized with a quaternary ammonium group; wherein the dextran polymer is a branched chain dextran polymer; wherein the branched chain dextran polymer comprises a plurality of glucose structural units; wherein 90 to 98 mol % of the glucose structural units are connected by a-D-1,6 linkages and 2 to 10 mol % of the glucose structural units are connected by a-1,3 linkages; wherein the quaternary ammonium group has formula (B)

(B)

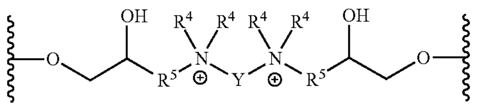

wherein

is a pendant oxygen on the dextran polymer; wherein each $R^4$ is independently selected from a substituted or unsubstituted $C_{1-6}$ alkyl group, each $R^5$ is independently selected from the group consisting of a $C_{1-6}$ alkanediyl group, and Y is a divalent bridging group selected from the group consisting of $C_{1-6}$ alkanediyl groups and a —$R^6$—O—$R^7$— group wherein $R^6$ and $R^7$ are independently selected from the group consisting of $C_{1-6}$ alkanediyl groups;

wherein the dextran polymer has a weight average molecular weight of 145,000 to 525,000 Daltons; and wherein the deposition aid polymer enhances deposition of the dermatologically acceptable oil from the cleansing formulation onto mammalian hair.

2. The hair care formulation of claim 1, wherein the hair care formulation is selected from the group consisting of a shampoo, a conditioning shampoo, a leave on hair conditioner and a rinse off hair conditioner.

3. The hair care formulation of claim 2, wherein the hair care formulation is selected from the group consisting of a shampoo and a conditioning shampoo.

4. The hair care formulation of claim 3, wherein the deposition aid polymer has a Kjeldahl nitrogen content corrected for ash and volatiles, TKN, of 0.5 to 4.5 wt %.

5. The hair care formulation of claim 4, further comprising a hair care cleansing surfactant.

6. The hair care formulation of claim 5, further comprising a chelating agent and a thickener.

7. The hair care formulation of claim 6, wherein the hair care cleansing surfactant comprises a mixture of sodium lauryl ether sulfate, cocamide monoethanolamine and cocamidopropyl betaine; wherein the chelating agent comprises tetrasodium ethylenediaminetetraacetic acid; and wherein the thickener comprises PEG-150 pentaerythrityl tetrastearate.

8. The hair care formulation of claim 7, further comprising a preservative.

9. A method of depositing oil on to mammalian hair, comprising:

selecting a hair care formulation according to claim 1;

applying the hair care formulation to mammalian hair.

* * * * *